United States Patent [19]

Lackey et al.

[11] Patent Number: 5,489,309
[45] Date of Patent: Feb. 6, 1996

[54] MODULAR HUMERAL COMPONENT SYSTEM

[75] Inventors: Jennifer Lackey, Memphis; Steven J. Imbimbo, Collierville, both of Tenn.; Robert Cofield, Rochester, Minn.

[73] Assignee: Smith & Nephew Richards Inc., Memphis, Tenn.

[21] Appl. No.: 500

[22] Filed: Jan. 6, 1993

[51] Int. Cl.$^6$ .................................................. A61F 2/40
[52] U.S. Cl. ................................................ 623/19; 623/18
[58] Field of Search ................................ 623/16, 18, 19, 623/20, 22, 23

[56] References Cited

U.S. PATENT DOCUMENTS

| | | | |
|---|---|---|---|
| 2,719,522 | 10/1955 | Huldack | 623/23 |
| 3,067,740 | 12/1962 | Haboush | 623/23 |
| 4,645,506 | 2/1987 | Link | 623/23 |
| 4,865,605 | 9/1989 | Dines et al. . | |
| 4,878,917 | 11/1989 | Kranz et al. . | |
| 4,895,572 | 1/1990 | Chernoff | 623/23 |
| 4,904,266 | 2/1990 | Barber . | |
| 4,919,670 | 4/1990 | Dale et al. . | |
| 4,995,883 | 2/1991 | Demane et al. . | |
| 5,002,580 | 3/1991 | Noble et al. . | |
| 5,030,234 | 7/1991 | Pappas et al. . | |
| 5,032,130 | 7/1991 | Schelhas et al. | 623/23 |
| 5,074,879 | 12/1991 | Pappas et al. . | |
| 5,080,676 | 1/1992 | May | 623/23 |
| 5,080,685 | 1/1992 | Bolesky et al. | 623/23 |
| 5,108,437 | 4/1992 | Kenna | 623/23 |
| 5,108,452 | 4/1992 | Fallin | 623/23 |
| 5,135,529 | 8/1992 | Paxson et al. | 623/23 |
| 5,181,928 | 1/1993 | Bolesky et al. | 623/23 |
| 5,314,479 | 5/1994 | Rockwood, Jr. et al. | 623/19 |

*Primary Examiner*—David Isabella
*Attorney, Agent, or Firm*—Pravel, Hewitt, Kimball & Krieger

[57] ABSTRACT

A modular humeral prosthesis that can be custom fitted to a particular patient by interchanging sizes of the various components by a surgeon interoperatively. The prosthesis features a humeral head having a hemispherically shaped outer surface for placement within the glenoid cavity of a human scapula, the head including on its undersurface a recessed center portion having a first cooperating connecting means. The body has a proximal end and a distal end, with the proximal end including an angled platform having a second cooperating connecting means for engagement with said first connecting means, and the distal end having a third cooperating connecting means. The body also includes a plurality of fins. A cylindrical primary stem has a proximal end and a distal end, the proximal end having a forth cooperating connecting means for engagement with said third connecting means, and the distal end having a fifth cooperating connecting means. A cylindrical secondary stem has a proximal end and a distal end, the proximal end having a sixth cooperating connecting means for engagement with said fifth connecting means, and the distal end having a tip for insertion within the medullary canal of a resected human humerus.

31 Claims, 4 Drawing Sheets

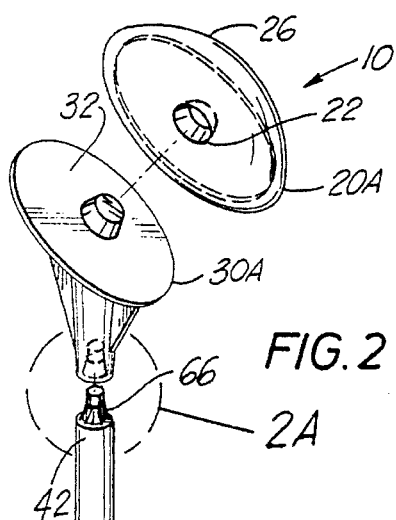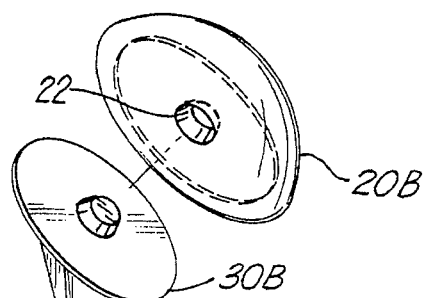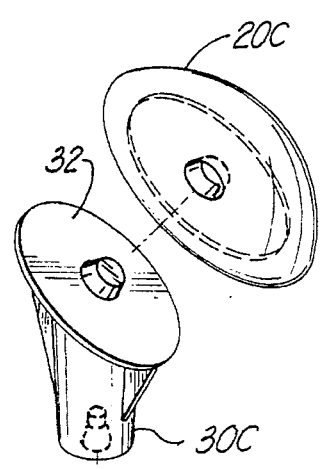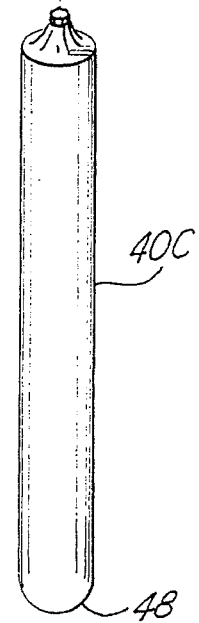

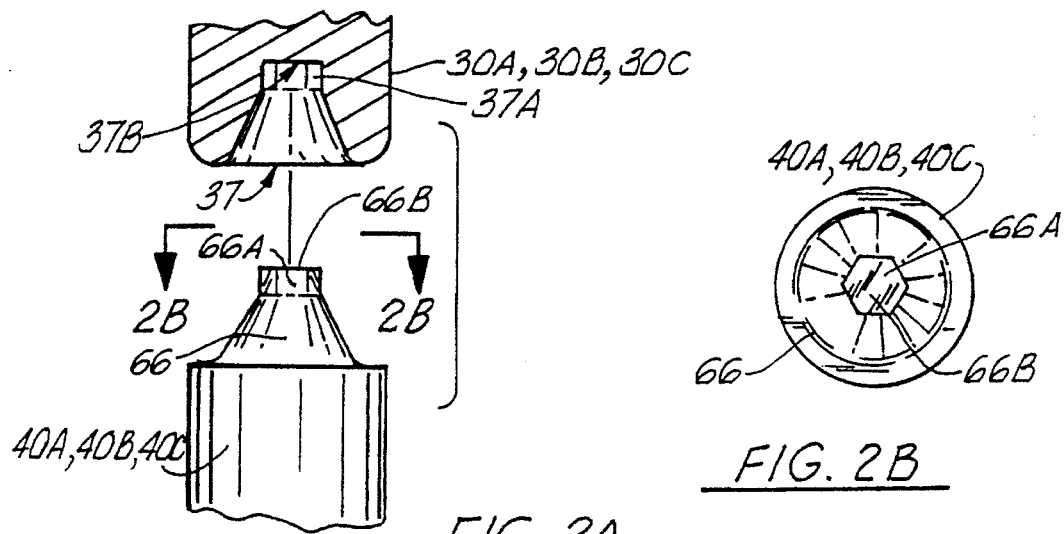
FIG. 2A
FIG. 2B
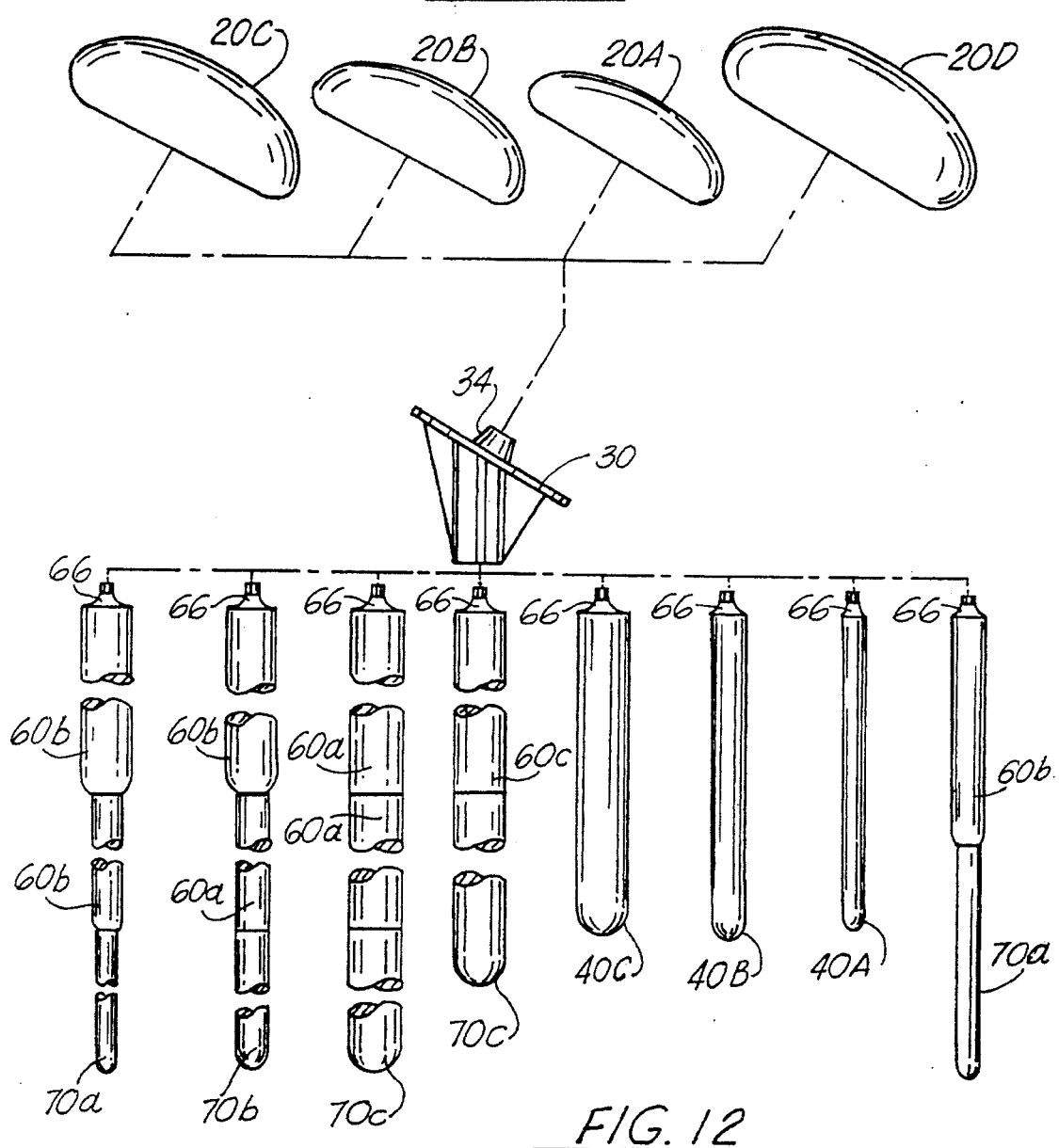
FIG. 12

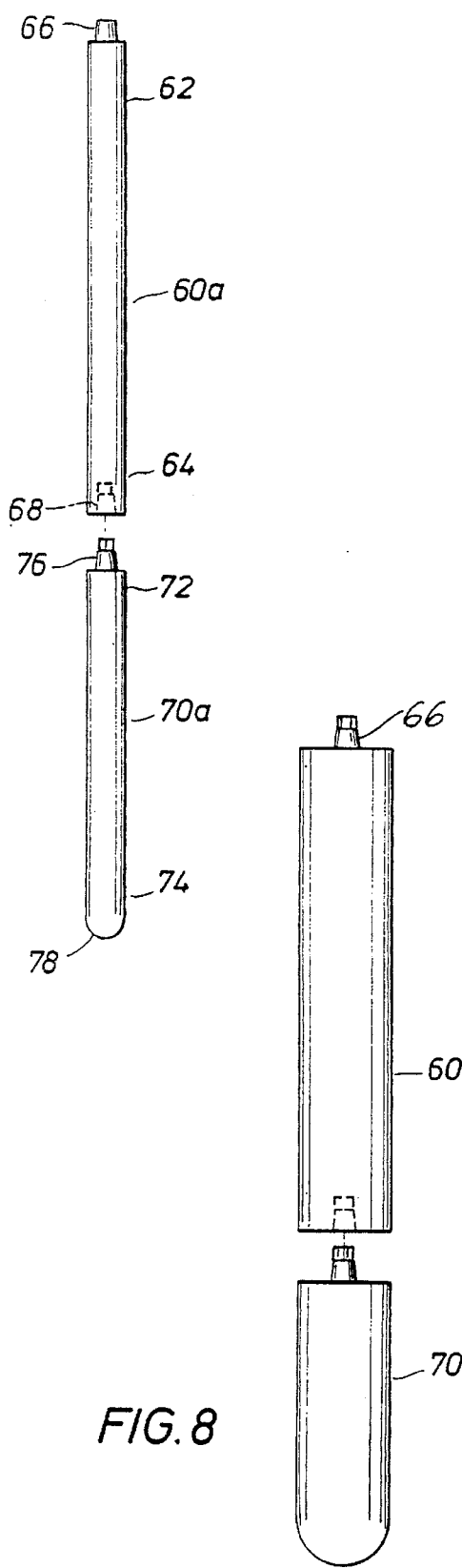
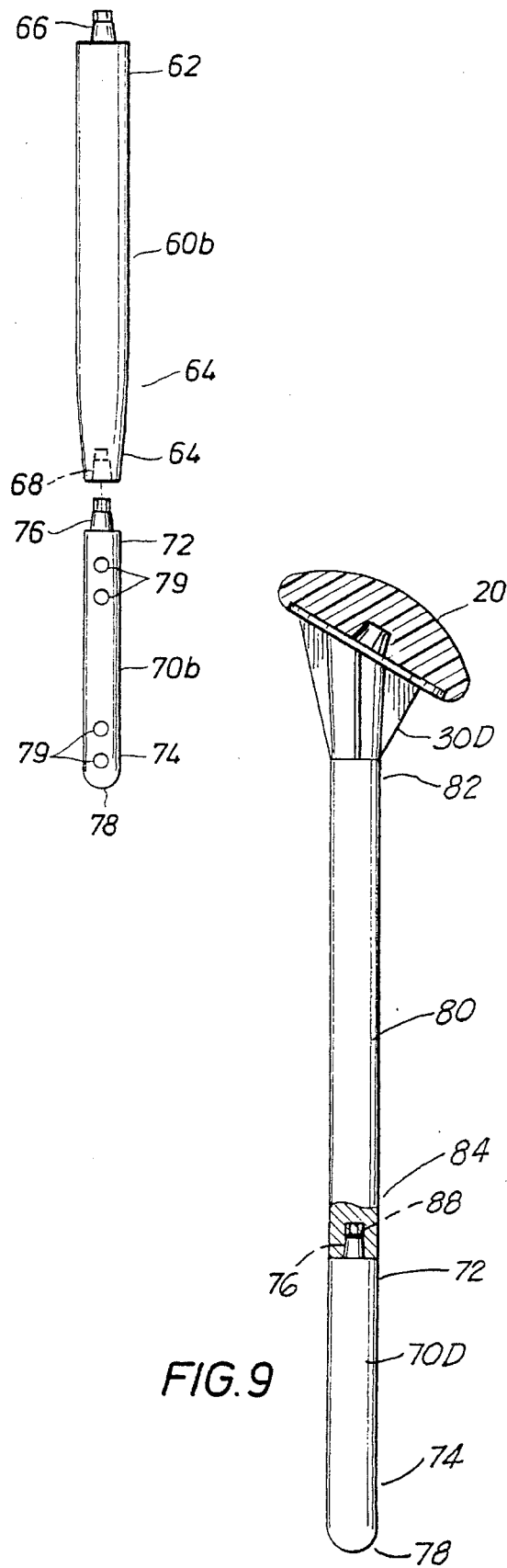
FIG. 6  FIG. 7  FIG. 8  FIG. 9

MODULAR HUMERAL COMPONENT SYSTEM

FIELD OF THE INVENTION

The present invention relates to an improved modular humeral prosthetic system where various component parts of the prosthetic implant can be selected during the surgical procedure in order to custom fit the implant to a patient, even in revision cases wherein components of differing diameters can connect together such as when proximal tissue is eroded with removal of the old prosthesis.

BACKGROUND OF THE INVENTION

Increasingly surgeons want to be able to custom fit humeral prosthesis to patients. Instead of having to choose a properly sized prosthesis from a group of preformed implants, it would be advantageous to have a basic design which can be modified with various component parts. This would eliminate the need to maintain a large inventory and would provide better fitting implants.

Custom fitted implants are particularly important in revision cases where an implant has to be removed and replaced. In this situation old cement must be removed and, in many cases, bone reabsorption occurs causing unpredictable proximal and/or distal bone loss or deformity which must be accommodated by the replacement prosthesis.

For initial implants, basic variations in patient anatomy are often confronted by the surgeon. Known humeral prosthetic implants do not achieve true anatomic compatibility with the proximal end of the humerus and do not provide the capability for modification of the humeral head size during surgery other than by replacement of the entire implant. Some patients have humeral necks that can be significantly longer or shorter than others. Also, shaft defects, which are not uncommon, are often not discovered until surgery. Variations in intramedullary canal diameter can also occur, which if not accompanied by a properly sized implant, can result in distal toggle. Currently available modular heads only fill the joint space of the glenoid cavity and not the proximal humeral bone cavity. Additionally, a patient's humeral anatomy can exhibit a wide proximal humeral cavity with a distal medullary canal that is half the size. Current humeral prosthesis do not allow for this type of mismatch.

Prior humeral prosthetic implants in use have a stem portion for implantation within the medullary canal of a human humerus and a head portion for engagement within the glenoid cavity of the human scapula. Such implants do not, however, achieve true anatomic compatibility with the proximal end of the human humerus, and do not provide a capability for modification of the stem during surgery other than by replacement of the entire implant.

A modular humeral prosthesis is known which is formed of a humeral stem and a head component which is readily attachable and detachable to and from each other for allowing intraoperative modifications of the implant. U.S. Pat. No. 4,919,607 entitled "Modular Humeral Prosthesis" issued to Dale et al. describes a modular prosthetic device which is anatomically compatible with the proximal human humerus and scapula and provides a modular head mechanism that can be interchangeable. U.S. Pat. No. 4,865,605 entitled "Modular Shoulder Prosthesis" issued to Dines et al describes a shoulder prosthesis which includes a humeral component and a glenoid component. These patents describe modular prosthesis which have only a head component and a stem component.

None of these modular humeral components address the problem of proximal humeral canal fill or variations in intramedullary canal diameter or length. This problem frequently occurs in revision cases wherein bone cement held an older prosthesis. The multiple part modular system of the present invention allows a surgeon to exchange parts intraoperatively to achieve optimal fixation of a humeral prosthesis, such as in revision cases wherein bone cement causes bone tissue removal upon removal of an earlier prosthesis.

The object of the invention therefore is to provide modular humeral prosthetic components which are anatomically compatible with the scapula, the proximal humerus and the distal stem portion of the humerus.

Another object of the invention is to provide a modular humeral prosthetic system of component parts which reduces the number of standard components and custom devices needed to achieve optimal fixation.

SUMMARY OF THE INVENTION

The present invention solves the problems discussed above by providing modular humeral prosthetic components which can be custom fitted to a particular patient by a surgeon prior to and during surgical insertion of the prosthesis. The component parts allow the surgeon to exchange the pieces intraoperatively to achieve optimal fixation.

The prosthesis includes a head which lies in the glenoid cavity, a body that is placed in the proximal end of the humerus, and a primary and secondary stem which fits in the humeral canal. The head attaches to a platform on the proximal end of the body and the primary stem attaches to the distal end of the body with a male/female locking mechanism. The secondary stem attaches to the primary stem with male/female locking mechanism. In a preferred embodiment the male/female locking mechanism is anti-rotational.

The head has a hemispherically shaped outer surface that fits within the glenoid cavity of a human scapula. The undersurface of the head has a recessed center portion which contains a female locking mechanism for connecting with a male locking mechanism on the platform at the proximal end of the body. The recessed center allows the platform to fit within the humeral head.

The body is a unitary cone shaped structure with the conical flare extending from its distal end. The platform mounted on the proximal end of the body is generally circular. A male locking mechanism is centrally located on the platform for connecting with the head of the modular humeral prosthesis. The platform is angled relative to the central longitudinal axis of the body. Mounted on the body are four fins which run from the distal portion of the body to the platform at the proximal end. These four fins are evenly spaced along the axis of the body. The distal end of the body has a female locking mechanism for connecting with the male locking mechanism on the primary stem.

The primary stem of the modular humeral component system is cylindrical and has a proximal end with a male locking mechanism for connection with the distal end of the body. The distal end of the stem may have either a tip for insertion into the medullary canal of a resected human humerus or a female locking mechanism for connecting to a secondary stem.

The secondary stem is cylindrical and has a proximal end with a male locking mechanism for connecting to the primary stem and a rounded or bullet shaped tip at its distal end. The primary and secondary stem may have transverse bores or slots extending through the stem to receive fixation screws.

In a preferred embodiment, the modular humeral components are made from a biocompatable material. The head may come in a variety of sizes, both in height and diameter. The body may come in a variety of cross-sectional diameter sizes and in a preferred embodiment the platform diameter of the various body sizes is generally uniform. The primary and secondary stems of the system may come in a variety of lengths and diameter sizes and the distal ends may be either bullet shaped or rounded, or squared off with a female locking mechanism. The male/female locking mechanism on all the body/stem components is of the same diameter and may have a two-way connection such that the components can be used as left or right side implants. In a preferred embodiment of the system, all of the component parts are interchangeable.

In an alternate embodiment, the body and primary stem may be one piece with the distal end of the stem having a female locking mechanism for connecting to a secondary stem. In another alternate embodiment, the body and primary stem may be one piece but of a smaller cross-sectional diameter for use in the humerus of a child or small adult.

BRIEF DESCRIPTION OF THE DRAWINGS

The objects, advantages and features of the invention will become more apparent when the detailed description of exemplary embodiments is considered in conjunction with the appended drawings, in which:

FIGS. 2–4 are perspective exploded views illustrating the preferred embodiment of the apparatus of the present invention in different stem diameters;

FIG. 2A is an enlarged fragmentary view of the preferred embodiment of the apparatus of the present invention illustrating the respective cooperating connector portions between adjacent components;

FIG. 2B is a section view taken along lines 2B—2B of FIG. 2A;

FIG. 5 is a perspective view illustrating an alternate embodiment of the apparatus of the present invention for use with small children;

FIG. 6 is a fragmentary view of the preferred embodiment of the apparatus of the present invention illustrating primary and secondary stem portions;

FIG. 7 is a fragmentary view of the preferred embodiment of the apparatus of the present invention illustrating a primary and secondary stem portions;

FIG. 8 is a fragmentary view of primary and secondary stem portions for use with the preferred embodiment of the apparatus of the present invention;

FIG. 9 is a partial sectional view of the preferred embodiment of the apparatus of the present invention;

FIG. 12 is an exploded plan view of the preferred embodiment of the apparatus of the present invention.

DETAILED DESCRIPTION OF A PREFERRED EMBODIMENT

Figure 1:
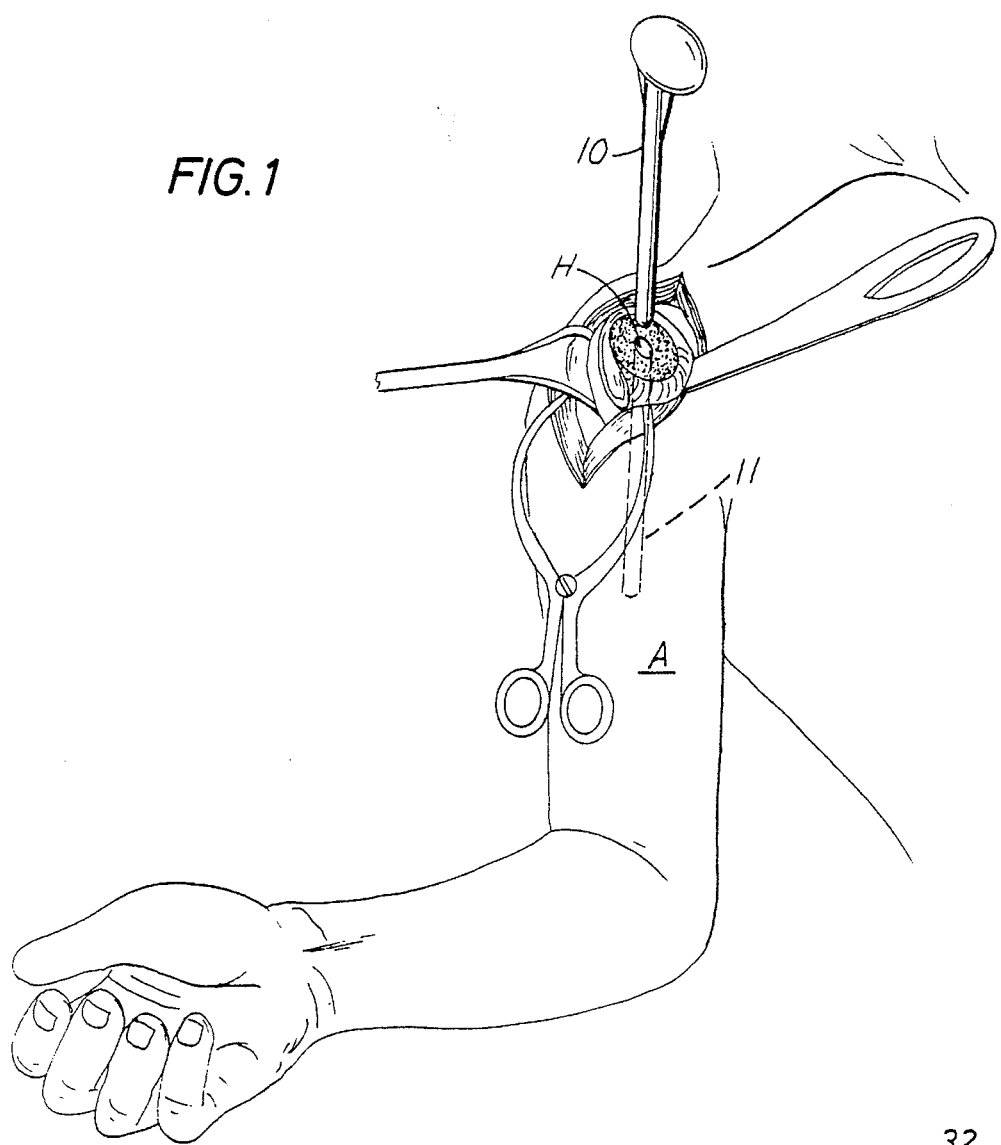
FIG. 1 is a frontal view of a modular humeral prosthesis according to the present invention as shown being implanted in the medullary canal of a human humerus.

Referring to FIG. 1, reference letter A identifies the arm of a patient which has been surgically opened to expose the humerus H. A modular humeral prosthesis 10 is being implanted into the humerus H. A dotted line 11 illustrates the path of the humeral prosthesis 10 as it is implanted into the humerus H of the patient.

As shown in FIG. 2, the modular humeral prosthesis 10 has a head 20A, a body 30A, and a primary stem 40A. The head 20A has a hemispherically shaped outer surface 26 for placement within the glenoid cavity of a human scapula, the outer spherical surface 26 being, for example, less than half the surface of a complete sphere.

Figure 10:
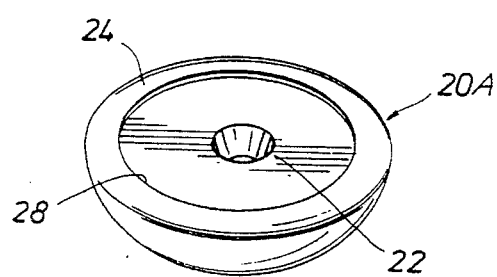
FIG. 10 is a fragmentary perspective view of the preferred embodiment of the apparatus of the present invention showing the prosthesis head portion thereof.

As shown in FIG. 10, the undersurface 24 of the head 20A has a recessed center 28 which contains a centrally located female locking mechanism 22 for engagement with a correspondingly shaped male locking mechanism 34 on a platform 32 of body 30A of the modular humeral prosthesis 10. The recessed center 28 allows the platform 32 of the body 30A to fit within the head 20A.

Figure 11:
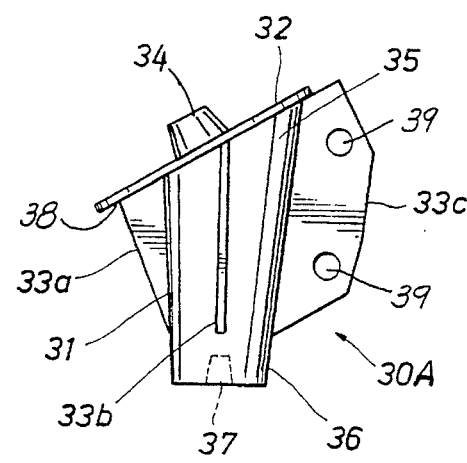
FIG. 11 is a fragmentary side view of the preferred embodiment of the apparatus of the present invention showing the body portion thereof.

Body 30A of the modular humeral prosthesis 10 has a proximal end 35 and a distal end 36 (see FIG. 11). The body 30A is a unitary, generally cone shaped structure with the conical flare extending from the distal end 36 of the body 30A to its proximal end 35. A generally circular platform 32 is mounted on the proximal end 35 of the body 30A. The platform 32 is angled relative to the central longitudinal axis of the body 30A and an attached cylindrical stem 40A (see FIGS. 2 and 9).

The platform 32 has a centrally located male locking mechanism 34 for engagement with the female locking mechanism 22 of the head 20A. The platform 32 also prevents the modular humeral prosthesis 10 from subsiding within the medullary canal of the humerus H. Body 30A has four fins 33 which are preferably evenly spaced circumferentially along the central longitudinal axis of the body 30A. As best shown in FIG. 11, fins 33 have one side 31 integral with the body 30 and extend a predetermined length distally from the underside 38 of the platform 32. Fins 33 extend outwardly to restrict rotational movement of the implant. Fin 33A is on the medial side of the body portion 30 and fins 33B and 33D (not shown) extend from the mid-line of body portion 30. Fin 33C extends from the lateral side of body portion 30. The fins 33A, B, and D are generally triangular in shape and do not extend beyond the diameter of the platform 32. The lateral fin 33C does extend a distance beyond the diameter of the platform 32 and is of a greater dimension than fins 33A, 33B and 33D.

When modular humeral prosthesis 10 is implanted in the humerus H, the lateral fin 33C preferably resides in the area posterior to the bicipital grove in the greater tuberosity of the humerus H. The lateral fin 33C may also have fixation holes 39 which aid in the fixation of the modular humeral prosthesis 10 after implantation in the humerus H.

As shown in FIG. 2, the primary stem 40A is an elongated cylinder having a linear axis defining a proximal end 42 and a distal end 44. The proximal end 42 of the primary stem 40A has a male locking mechanism 66 for engagement with the female locking mechanism 37 on the distal end 36 of the body 30A. The distal end 44 of primary stem 40A has a rounded or bullet shaped tip 48 for insertion into the medullary canal of a resected humerus H.

FIG. 3 and FIG. 4 show two different sizes (i.e., different diameters) of the modular humeral prosthesis 10. The cross-sectional diameter of the body 30B is greater than the cross-sectional diameter of the body 30A and the cross-sectional diameter of 30C is greater than the cross-sectional diameter of the body 30B. However, the dimensions of the platform 32 of the bodies 30A, 30B and 30C are generally the same. Likewise, the primary stem 40B and 40C is of a greater cross-sectional diameter than primary stem 40A. The heads 20B and 20C are also of differing dimensions. It should be understood however, that while a number of different size heads, bodies, and stems are provided, the sizes of male and female connectors 34, 22 remain the same between head components and body components of different size. Similarly, the locking mechanisms 37, 66 are the same size and configuration for different sizes of head and stem components. The locking components 68, 76 are also the same size and configuration for different diameter and different length stems. This allows components of different diameters to be connected together, such as in revision cases, wherein the proximal humerus may have been enlarged because of the earlier use of bone cement to secure a previous prosthesis.

In FIG. 2A and 2B, female 37 and male 66 connectors are shown as conically shaped with hexagonal portions 37A, 66A to prevent rotation between components. When the connections are made between the various female/male connectors (illustrated by the female 37 and male 66 connectors), as the various components are assembled using a mall or an impact driver, an interference or wedge lock fit is formed. The coordinating transverse surface 37B of the female connector 37 and the coordinating transverse surface 66B of the male connector 66 will be slightly spaced apart upon complete assembly of the connectors 37 and 66 so that a full interference or wedge lock fit can be achieved.

FIGS. 6, 7 and 8 show an alternate embodiment of the primary stem 40A, plus a secondary stem 70A, 70B and 70C. As shown in FIG. 6, a primary stem 60A has a proximal end 62 and a distal end 64. At the proximal end 62 is a male locking mechanism 66 for engagement with the female locking mechanism 37 on the body 30A. At the distal end 64 is a female locking mechanism 68 for engagement with a male locking mechanism 76 on the secondary stem 70A. The secondary stem 70A has a proximal end 72 and a distal end 74. The proximal end 72 has a male locking mechanism 76 for engagement with the female locking mechanism 68 on the distal end 64 of the primary stem 60A. The distal end 74 has a rounded or bullet shaped tip 78 for insertion into the medullary canal of a resected humerus H.

In FIG. 7, another alternate embodiment of the present invention is shown. A primary stem 60B has a distal end 64 with a female locking mechanism 68. A secondary stem 70B, having a smaller cross-sectional diameter, may connect to the primary stem 60B having a greater cross-sectional diameter. The secondary stem 70B is shown with transverse bores or slots 79 extending through it. The bores or slots 79 receive fixation screws in order to maintain fragmented bone segments in a relative stable alignment with one another. Thus, the present invention allows custom replacement of the proximal humerus with simultaneous repair of the distal humerus using bone screws that fit one or more bores or slots 79. In an alternate embodiment not shown, the bores or slots 79 may be placed on the primary stem 40A and its alternate embodiments or on the secondary stems 70A, C, and D.

FIG. 8 illustrates a primary stem 60C and a secondary stem 70C of a greater cross-sectional diameter than either the primary stem 60A or 60B or the secondary stem 70A or 70B.

Another alternate embodiment of the present invention can be seen in FIG. 5, where the body 30A and stem 40A is combined in a one piece stem 50 of a very small cross-sectional diameter having a proximal end 52 and a distal end 53. In this alternate embodiment, the proximal end 52 has a plurality of fins 54 and a platform 51. The fins 54 are evenly spaced along the axis of the stem 50 and the fins 54 have one side 58 integral with the stem 50 and extend a predetermined length distally from the platform 51. The fins 54 extend outwardly to restrict rotational movement of the implant. One fin 54 is on the medial side of the stem 50, two of the fins 54 extend from the mid-line of the stem 50, and another fin 54 extends from the lateral side of the stem 50. The fins 54 are generally triangular in shape and do not extend beyond the diameter of the platform 52. A male locking mechanism 55 is centrally located on the platform 51 of the stem 50 for engagement with the female locking mechanism 22 of the head 20D. Any of the heads 20A–D will fit on the platform 51. The distal end 53 has a rounded or bullet shaped tip 56 for insertion into the medullary canal of a resected humerus H. The stem 50 is of a small cross-sectional diameter in order to accommodate the humerus of a child or a small adult.

A further alternate embodiment is shown in FIG. 9, where the body 30A and stem 60A is combined in a one piece primary stem 80 with a secondary stem 70D. The primary stem 80 and secondary stem 70D can be of the same cross-sectional diameters as those shown in the primary stems 60A–C and the secondary stems 70A–C. The primary stem 80 has a proximal end 82 and a distal end 84. At the proximal end 82 is a body portion 30D identical to the body 30 as illustrated in FIG. 11 but without the female locking mechanism 37. At the distal end 84 is a female locking mechanism 88 for engagement with a male locking mechanism 76 on the secondary stem 70D. The secondary stem 70D has a has a proximal end 72 and a distal end 74. The proximal end 72 has a male locking mechanism 76 for engagement with the female locking mechanism 88 of the distal end 84 of the primary stem 80. The distal end 74 has a rounded or bullet shaped tip 78 for insertion into the medullary canal of a resected humerus H.

In a preferred embodiment of the present invention, as shown in FIG. 12, the modular humeral component system includes a plurality of heads 20 of different sizes; a plurality of bodies 30 in a variety of cross-sectional diameters; and a plurality of primary stems 40 and 60, and secondary stems 70 having different lengths and diameters with both rounded distal ends 48 and 78 and squared off distal ends 68. The connections between the head 20 and the body 30 are achieved by a male/female locking mechanism which is identical in size and shape among all the component parts of the system. The primary stem 40 and 60, and the secondary stem 70 have a different identical male/female locking mechanism. All of the various sizes of the head 20, the body 30, the primary stem 40 and 60, and the secondary stem 70 are interchangeable among each other. These compatible modular humeral components, which may be supplied in a kit, allow a surgeon to exchange parts intraoperatively in order to achieve optimal fixation in humeral prosthetic implant procedures, such as in revision cases wherein differing diameters of stems 60b and 70a are needed, for example.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed is:

1. A modular humeral prosthesis kit apparatus that can be custom fitted to a particular patient by a surgeon interoperatively, comprising:

a) multiple humeral head portions, each having a hemispherically shaped outer surface for placement within the glenoid cavity of a human scapula, a planar undersurface and a socket that communicates with undersurface;

b) a plurality of modular body portions each having a proximal end, a distal end, a generally cylindrically shaped stem portion having a central longitudinal axis, and a male projecting portion that forms a taper-lock connection with the socket of a selected head portion;

c) each said proximal end including an angled platform having a diameter and at least one radially extending projection that connects between the platform and stem portion for restricting rotational movement of the prosthesis during use;

d) the generally cylindrically shaped portion extending from the platform to a position well away from the fin;

e) said distal end of the stem portion having a connecting means, the respective body portions being of variable lengths between the proximal and distal end;

f) wherein there are multiple cylindrical primary modular stem members, each having a proximal end and a distal end;

g) multiple cylindrical secondary modular stem members each having a proximal end and a distal end;

h) an end of each of said primary and secondary stem members having cooperating first and second connecting means for engagement with corresponding connecting means of a selected body portion or stem member, at least one of said distal ends having a tip for insertion within the medullary canal of a resected human humerus; and i) a selected number of components selected from said humeral head portions, body portions, primary stem portions, and secondary stem portions being affixable together end to end thereby forming a modular prosthesis that can be custom fitted to a particular patient by selectively interchanging different diameter sizes of the head portions, body portions, and stems to fit a prosthesis to the patient.

2. The modular humeral prosthesis of claim 1, wherein the humeral head is generally hemispherically shaped.

3. The modular humeral prosthesis of claim 1, wherein the body is a unitary structure and the connecting means is a conically-shaped portion.

4. The modular humeral prosthesis of claim 1, wherein the platform is angled relative to the central longitudinal axis of the body cylindrically shaped portion.

5. The modular humeral prosthesis of claim 1, wherein the reinforcement means comprises at least one fin.

6. The modular humeral prosthesis of claim 5, wherein the fin is integral with the body.

7. The modular humeral prosthesis of claim 5, wherein the fin extends outwardly of the cylindrical portion for restricting rotational movement of the prosthesis during use.

8. The modular humeral prosthesis of claim 5, wherein the fin has at least one fixation hole.

9. The modular humeral prosthesis of claim 1, wherein at least one of the primary stems has a tip for insertion into the medullary canal of a resected human humerus.

10. The modular humeral prosthesis of claim 1, wherein, the primary stem has a taper at its distal end.

11. An implantable modular humeral prosthesis that can be custom fitted to a particular patient by a surgeon interoperatively, comprising:

a) a humeral head portion having a hemispherically shaped outer surface for placement within the glenoid cavity of a human scapula and an undersurface for engagement with a body portion, said head portion including on its undersurface a conically shaped socket that defines a first cooperating connecting means;

b) a cylindrically-shaped body portion that is of a generally uniform diameter said body portion having a proximal end and a distal end, said proximal end including a platform having a conically shaped projecting portion that defines a second cooperating connecting means for engagement with said first connecting means for forming a taper lock connection therewith;

c) reinforcement means extending between said cylindrically-shaped body portion and said angled platform, said reinforcement means including at least one radially extending projection for restricting rotational movement of the prosthesis during use;

d) a primary stem portion having a proximal end and a distal end, said proximal end having a fourth cooperating connecting means for engagement with said third connecting means, said distal end having a fifth cooperating connecting means;

e) a secondary stem portion having a proximal end and a distal end, said proximal end having a sixth cooperating connecting means for engagement with said fifth connecting means, said distal end having a tip for insertion within the medullary canal of a resected human humerus; and f) the said humeral head portion, body portion, primary stem portion, and secondary stem portion being coupled together thereby forming a modular prosthesis that can be custom fitted to a particular patient by interchanging sizes of the various selected humeral head, body portion, and stem portion components.

12. The modular humeral prosthesis of claim 1 or 11, wherein at least one of the stem members have transverse bores extending therethrough to receive fixation screws in order to maintain fragmented bone segments in relative stable alignment with one another.

13. The modular humeral prosthesis of claim 1 or 11, wherein at least one of the stem members have transverse slots extending therethrough to receive fixation screws in order to maintain fragmented bone segments in relative stable alignment with one another.

14. The modular humeral prosthesis of claim 1 or 11, wherein the cooperating connecting means is formed with rotational restraint means.

15. An implantable modular humeral prosthesis that can be custom fitted to a particular patient by a surgeon interoperatively, comprising:

a) a humeral head portion having a convex-shaped outer surface for placement within the glenoid cavity of a human scapula and an undersurface for engagement with a body portion, said head portion including on its undersurface a recessed center socket portion having a first cooperating connecting means;

b) a cylindrically-shaped primary stem portion of generally uniform diameter having a proximal end and a distal end, said proximal end having an angled platform and at least one radial projection for resisting rotational movement of the prosthesis during use, said angled platform having a conically-shaped projection that defines a second cooperating connecting means for engagement with said first connecting means, said distal end having a third cooperating connecting means;

c) a cylindrical secondary stem portion having a proximal end and a distal end, said proximal end having a fourth cooperating connecting means for engagement with said third connecting means, said distal end having a tip for insertion within the medullary canal of a resected human humerus;

d) the said humeral head portion, primary stem portion, and secondary stem portion being coupled together thereby forming a modular prosthesis that can be custom fitted to a particular patient by interchanging sizes of the various components.

16. The modular humeral prosthesis of claim 15, wherein the humeral head is generally hemispherically shaped.

17. The modular humeral prosthesis of claim 15, wherein the recessed center portion on the undersurface of the head allows the platform of the body to fit within the humeral head.

18. The modular humeral prosthesis of claim 15, wherein the body is a unitary structure with a conically-shaped portion extending proximally from the distal end of the body.

19. The modular humeral prosthesis of claim 15, wherein the platform is angled relative to the central longitudinal axis of the body portion.

20. The modular humeral prosthesis of claim 15, further comprising at least one fin extending from the body portion beyond the periphery of the platform.

21. The modular humeral prosthesis of claim 15, wherein the fin has one side integral with the body portion and extends a predetermined length distally from the platform.

22. The modular humeral prosthesis of claim 20, wherein there are a plurality of fins including one fin on the medial side of the primary stem, a second and third fin extending from the midline of either side of the primary stem and a forth fin extending from the lateral side of the primary stem.

23. The modular humeral prosthesis of claim 22, wherein the outward extension of at least a plurality of the fins is no greater than the diameter of the platform.

24. The modular humeral prosthesis of claim 20, wherein one fin has at least one fixation hole.

25. The modular humeral prosthesis of claim 15, wherein the primary stem and secondary stem have transverse bores extending therethrough to receive fixation screws in order to maintain fragmented bone segments in relative stable alignment with one another.

26. The modular humeral prosthesis of claim 15, wherein the primary stem and secondary stem have transverse slots extending therethrough to receive fixation screws in order to maintain fragmented bone segments in relative stable alignment with one another.

27. An implantable modular humeral prosthesis that can be custom fitted to a particular patient by a surgeon interoperatively, comprising:

a) a humeral head portion having a hemispherically shaped outer surface for placement within the glenoid cavity of a human scapula and an undersurface having a conical socket connector for receiving a body portion;

b) a stem having a cylindrical portion of substantially uniform diameter, a proximal end and a distal end, said proximal end having a body portion including an angled platform and at least one fin, for resisting rotational movement of the prosthesis during use, said angled platform having a conical projecting cooperating connecting means for engagement with said connecting means, said platform being sized and shaped to fit said conical socket of said humeral head portion, said distal end having a tip for insertion within the medullary canal of a resected human humerus;

c) the stem portion being of a very small cross-sectional diameter to accommodate the humerus of a child or a small adult, the platform being of a much larger diameter than the stem portion; and d) the humeral head portion and stem portion being coupled together thereby forming a modular prosthesis that can be custom fitted to a particular patient by interchanging sizes of the head portion.

28. The modular humeral prosthesis of claim 1 or 11, wherein the connecting means cooperates by means of an interference fit.

29. The modular humeral prosthesis of claim 15 or 27, wherein the connecting means cooperates by means of an interference fit.

30. The modular humeral prosthesis of claim 1 or 11, wherein the connecting means cooperates by means of a wedge lock fit.

31. The modular humeral prosthesis of claim 15 or 27, wherein the connecting means cooperates by means of a wedge lock fit.

* * * * *